(12) United States Patent
Davis et al.

(10) Patent No.: US 6,602,683 B1
(45) Date of Patent: Aug. 5, 2003

(54) BIOLOGICALLY ACTIVE EPH FAMILY LIGANDS

(75) Inventors: Samuel Davis, New York, NY (US); Nicholas W. Gale, Tarrytown, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 234 days.

(21) Appl. No.: 09/051,994

(22) PCT Filed: Oct. 25, 1996

(86) PCT No.: PCT/US96/17201

§ 371 (c)(1),
(2), (4) Date: Apr. 24, 1998

(87) PCT Pub. No.: WO97/15667

PCT Pub. Date: May 1, 1997

Related U.S. Application Data

(60) Provisional application No. 60/007,015, filed on Oct. 25, 1995.

(51) Int. Cl.[7] .............................................. C12N 15/00
(52) U.S. Cl. ................... 435/69.1; 435/320.1; 435/325; 536/235; 530/350
(58) Field of Search .............................. 435/69.1, 320.1, 435/325; 536/23.5; 530/350

(56) References Cited

FOREIGN PATENT DOCUMENTS

| WO | WO94/11384 A | | 5/1994 |
|---|---|---|---|
| WO | WO 9704091 | * | 2/1997 |
| WO | WO 9736919 | * | 10/1997 |
| WO | WO 9740153 | * | 10/1997 |

OTHER PUBLICATIONS

Hillier et al, The WashU–Merck EST project, Genbank Accession NO. H10006, Jun. 23, 1995.*
Gale et al., Oncogene 13:1343–1352, Sep. 19, 1996.*
Tang et al., Genomics 41:17–24, 1997.*
Hillier et al, The WashU–Merck EST project, Genbank Accession No. H10006.*
Gale et al., Oncogene 13:1343–1352.*
Tang et al., Genomics 41:17–24.*
EMBL/Genbank/DDBJ databases, Jul. 31, 1996, Accession No. HSU57001, Cerreti D.P. XPOO2025757.

* cited by examiner

Primary Examiner—Yvonne Eyler
Assistant Examiner—Eliane Lazar-Wesley
(74) Attorney, Agent, or Firm—Laura J. Fischer; Linda O. Palladino; Robert J. Cobert

(57) ABSTRACT

A novel ligand (Efl-6) that binds the Elk subfamily of Eph receptors is identified, and methods for making the soluble Elf-6 ligand in biologically active form is described. A cDNA clone encoding this novel protein enables production of the recombinant protein, which is useful to support neuronal and other eph receptor-bearing cell populations.

14 Claims, 6 Drawing Sheets

FIGURE 1A

```
           10         20         30         40         50         60         70         80
            *          *          *          *          *          *          *          *
GAATTCCCAC CCCGGGATCT GTGAGACTGA GCGCTCTGCC GCGGGGGCGC GGGCACAGCA GGAARCAGGT CCGCGTGGGC
CTTAAGGGTG GGGCCCTAGA CACTCTGACT CGCGAGACGT CGCCCCCGCG CCCGTGTCGT CCTTYGTCCA GGCGCACCCG 90        100        110        120        130        140        150        160
            *          *          *          *          *          *          *          *
GCTGGGGGCA TCAGCTACCG GGGTGGTCCG GGCTGAAGAG CCAGGCAGCC AAGGCAGCCA CCCCGGGGGG TGGGCGACTT
CGACCCCCGT AGTCGATGGC CCCACCAGGC CCGACTTCTC GGTCCGTCGG TTCCGTCGGT GGGGCCCCCC ACCCGCTGAA 170        180        190        200        210        220        230
            *          *          *          *          *          *          *
TGGGGAGTT GGTGCCCCGC CCCCCAGGCC TTGGCGGGGT C ATG GGG CCC CAT TCT GGG CCG GGG GGC
ACCCCCTCAA CCACGGGGCG GGGGGTCCGG AACCGCCCCA G TAC CCC GGG GTA AGA CCC GGC CCC CCG
                                             M   G   P   H   S   G   P   G   G>

240        250        260        270        280        290
            *          *          *          *          *          *
GTG CGA GTC GGG GCC CTG CTG CTG GGG GTT TTG GGG CTG GTG TCT GGG CTC AGC CTG GAG CCT
CAC GCT CAG CCC CGG GAC GAC GAC CCC CAA AAC CCC GAC CAC AGA CCC GAG TCG GAC CTC GGA
 V   R   V   G   A   L   L   L   G   V   L   G   L   V   S   G   L   S   L   E   P>

300        310        320        330        340        350        360
     *          *          *          *          *          *          *
GTC TAC TGG AAC TCG GCG AAT AAG AGG TTC CAG GCA GAG GGT TAT GTG CTG TAC CCT CAG ATC
CAG ATG ACC TTG AGC CGC TTA TTC TCC AAG GTC CGT CTC CCA ATA CAC GAC ATG GGA GTC TAG
 V   Y   W   N   S   A   N   K   R   F   Q   A   E   G   Y   V   L   Y   P   Q   I>
```

FIGURE 1B

```
     370         380         390         400         410         420
      *           *           *           *           *           *
GGG GAC CGG CTA GAC CTG CTC TGC CCC CGG GCC CGG CCT CAC TCC CCT AAT TAT
CCC CTG GCC GAT CTG GAC GAG ACG GGG GCC CGG GCC GGA GTG AGG AGA TTA ATA
 G   D   R   L   D   L   L   C   P   R   A   R   P   H   S   P   N   Y>

430         440         450         460         470         480         490
      *           *           *           *           *           *           *
GAG TTC TAC AAG CTG TAC CTG GTA GGG GGT GCT CAG CGC GCC CCC CCT GCC CCA
CTC AAG ATG TTC GAC ATG GAC CAT CCC CCA CGA GTC GCG CGG GGG GGA CGG GGT
 E   F   Y   K   L   Y   L   V   G   G   A   Q   R   A   P   P   A   P>

500         510         520         530         540         550         560
      *           *           *           *           *           *           *
AAC CTC CTT CTC ACT TGT GAT CGC CCA GAC CTC GAT TAC CAC GAT TTC CAG GAG TAT
TTG GAG GAA GAG TGA ACA CTA GCG GGT CTG GAG CTA ATG GTG CTA AAG GTC CTC ATA
 N   L   L   L   T   C   D   R   P   D   L   D   Y   H   D   F   Q   E   Y>

570         580         590         600         610         620
      *           *           *           *           *           *
AGC CCT AAT CTC TGG GGC CAC GAG TTC CGC TCG TAC ATC ATT GCC ACA TCG GAT
TCG GGA TTA GAG ACC CCG GTG CTC AAG GCG AGC ATG TAG TAA CGG TGT AGC CTA
 S   P   N   L   W   G   H   E   F   R   S   Y   I   I   A   T   S   D>

630         640         650         660         670         680         690
      *           *           *           *           *           *           *
GGG ACC CGG GAG GGC AGC CTG GAG CAC GGT GTG TGC CTA ACC AGA GGC ATG AAG GTG CTT
CCC TGG GCC CTC CCG TCG GAC CTC GTG CCA CAC ACG GAT TGG TCT CCG TAC TTC CAC GAA
 G   T   R   E   G   S   L   E   H   G   V   C   L   T   R   G   M   K   V   L>
```

FIGURE 1C

```
          700             710             720             730             740             750
           *               *               *               *               *               *
CTC C(A/G)A GTG GGA CAA AGT CCC CGA GGA GGG GCT GTC CCC CGA AAA CCT GTG TCT GAA ATG CCC ATG
GAG G(T/C)T CAC CCT GTT TCA GGG GCT CGA CAG GGG GCT GCT TTT GGA CAC AGA CTT TAC GGG TAC
 L   (Q/R)  V   G   Q   S   P   R   G   G   A   V   P   R   K   P   V   S   E   M   P   M>

760             770             780             790             800             810
           *               *               *               *               *               *
GAA AGA GAC CGA GGG GCA GCC CAC AGC CTG GAG CCT GGG AAG GAG AAC CTG CCA GGT GAC CCC ACC
CTT TCT CTG GCT CCC CGT GTG TCG GAC CTC GGA CCC TTC CTC TTG GAC GGT CCA CTG GGG TGG
 E   R   D   R   G   A   A   H   S   L   E   P   G   K   E   N   L   P   G   D   P   T>

820             830             840             850             860             870             880             890
           *               *               *               *               *               *               *               *
AGC AAT GCA ACC TCC CGG GGT GCT GAA GGC CCC CTG CCC CCT CCC AGC ATG CCT GCA GTG GCT GGG
TCG TTA CGT TGG AGG GCC CCA CGA CTT CCG GGG GAC TCG GGA GGG CCC TAC GGA CGT CAC CGA CCC
 S   N   A   T   S   R   G   A   E   G   P   L   P   P   P   S   M   P   A   V   A   G>

900             910             920             930             940             950
           *               *               *               *               *               *
GCA GGG GGG CTG GCG CTG CTC TTG GGC CTG GCA GGG GTG CAC CGG GGT GCC ATG TGT TGG CGG
CGT CCC CCC GAC CGC GAC GAG AAC CCG GAC CGT CCC CAC GTG GCC CCA CGG TAC ACA ACC GCC
 A   G   G   L   A   L   L   L   G   L   A   G   V   H   R   G   A   M   C   W   R>
```

FIGURE 1D

```
      960         970         980         990         1000        1010        1020
       *           *           *           *           *           *           *
AGA CGG CGG GCC CGG AAG CCT TCG GAG AGT CGC CAC CCT GGT CCT GGC TCC TTC GGG AGG GGA TCT
TCT GCC GCC CGG TTC GGA AGC CTC TCA GCG GTG GGA CCA GGA CCG AGG AAG CCC TCC CCC AGA
 R   R   R   A   R   K   P   S   E   S   R   H   P   G   P   G   S   F   G   R   G   S>

1030        1040        1050        1060        1070        1080
       *           *           *           *           *           *
CTG GGC CTG GGG GGT GGA GGT GCA GAT CCC TTC TGC CCC GGG ATG GGA CCT GGG GAG GCT GAG CTC CGG GAG CTC CGA GAT CCC TAT GCT
GAC CCG GAC CCC CCA CCT CTA CCT CGT GCC CGA CGA GGC CCG GGG CCG GGG GCC GGG CCC TAT TAC CCC GGA GCC CTC GAT CCC TAT CGA
 L   G   L   G   G   G   G   G   M   G   P   G   E   A   E   L   R   E   L   G   I   A>

1090        1100        1110        1120        1130        1140        1150
       *           *           *           *           *           *           *
CTG CGG GGT GGC GGG GCT GCA GAT CCC TTC TGC CCC CAC TAT GAG AAG GTG AGT GGT GAC TAT
GAC GCC CCA CCG CCG CGA CGT CTA GGG AAG ACG GGG GTG ATA CTC TTC CAC TCA CCA CTG ATA
 L   R   G   G   G   A   A   D   P   F   C   P   H   Y   E   K   V   S   G   D   Y>

1160        1170        1180        1190        1200        1210        1220
       *           *           *           *           *           *           *
GGG CAT CCT GTG TAT ATC GTG CAG GAT GGG CCC GGG CCC CAG AGC CCT CCA AAC ATC TAC AAG GTA
CCC GTA GGA CAC ATA TAG CAC GTC CTA CCC GGG GTC TCG GGA GGT TTG TAG ATG TTC CAT
 G   H   P   V   Y   I   V   Q   D   G   P   G   P   Q   S   P   P   N   I   Y   K   V>

1230        1240        1250        1260        1270        1280        1290        1300
       *           *           *           *           *           *           *           *
TGA GGGCTC CTCTCACGTG GCTATCCTGA ATCCAGCCCT TCTTGGGGTG CTCCTCCAGT TTAATTCCTG GTTTGAGGGA
ACT CCCGAG GAGAGTGCAC CGATAGGACT TAGGTCGGGA AGAACCCCAC GAGGAGGTCA AATTAAGGAC CAAACTCCCT
 *>
```

FIGURE 1E

```
          1310        1320        1330        1340        1350        1360        1370        1380
            *           *           *           *           *           *           *           *
CACCCTCTAAC ATCTCGGCCC CCTGTGCCCC CCCAGCCCCT TCACTCCTCC CGGCTGCTGT CCTCGTCTCC ACTTTTAGGA
GTGGAGATTG TAGAGCCGGG GGACACGGGG GGGTCGGGGA AGTGAGGAGG GCCGACGACA GGAGCAGAGG TGAAAATCCT 1390        1400        1410        1420        1430        1440        1450        1460
            *           *           *           *           *           *           *           *
TTCCCTAGGA TTCCCACTGC CCCACTTCCT GCCCTCCCGT TTGGCCATGG GTGCCCCCCT CTGTCTCAGT GTCCCTGGAT
AAGGAATCCT AAGGGTGACG GGGTGAAGGA CGGGAGGGCA AACCGGTACC CACGGGGGGA GACAGAGTCA CAGGGACCTA 1470        1480        1490        1500        1510        1520        1530        1540
            *           *           *           *           *           *           *           *
CCTTTTTCCT TGGGGAGGGG CACAGGCTCA GCCTCCTCTC TGACCATGAC CCAGGCATCC TTGTCCCCCT CACCCACCCA
GGAAAAAGGA ACCCCTCCCC GTGTCCGAGT CGGAGGAGAG ACTGGTACTG GGTCCGTAGG AACAGGGGGA GTGGGTGGGT 1550        1560        1570        1580        1590        1600        1610        1620
            *           *           *           *           *           *           *           *
GAGCTAGGGG CGGGAACAGC GTCTCTAGGT GTTGGCACCG CCTTCTTTCT GCCTCTCACT GGTTTCTTCT TCTCTATCTC
CTCGATCCCC GCCCTTGTCG CAGAGATCCA CAACCGTGGC GGAAGAAAGA CGGAGAGTGA CCAAAAGAGA AGAGATAGAG 1630        1640        1650        1660        1670        1680        1690        1700
            *           *           *           *           *           *           *           *
TTATTCTTTC CCTCTCTTCC GTCTCTAGGT CTGTTCTTCT TCCCTAGCAT CCTCCTCCCC ACATCTCCTT TCACCCTCTT
AATAAGAAAG GGAGAGAAGG CAGAGATCCA GACAAGAAGA AGGGATCGTA GGAGGAGGGG TGTAGAGGAA AGTGGGAGAA 1710        1720        1730        1740        1750        1760        1770        1780
            *           *           *           *           *           *           *           *
GGCTTCTTAT CCTGTGNCTC TCCCATCTCC TGGGTGGGGG TTTCTCCCCT TAGCTTTCAG CCCCCTTCTG
CCGAAGAATA GGACACNGAG AGGGTAGAGG ACCCACCCCC NATCAAAGCA NTAGTTTCGT AAAGAGGGA ATCGAAAGTC GGGGAAGAC
```

FIGURE 1F

```
        1790       1800       1810       1820       1830       1840       1850       1860
          *          *          *          *          *          *          *          *
ANCTCTCATA CCAANCACTC CCCTCAGTCT GTCAAAAATG GGGGGCTTAT GGGGAAGGGT CTGACAATCC ACCCCAGGTC
TNGAGAGTAT GGTTNGTGAG GGGAGTCAGA CAGTTTTTAC CCCCCGAATA CCCCTTCCCA GACTGTTAGG TGGGGTCCAG
```

BIOLOGICALLY ACTIVE EPH FAMILY LIGANDS

INTRODUCTION

This application is a national stage entry of PCT/US96/17201 filed Oct. 25, 1996 and claims priority to provisional application No. 60/007,015 filed Oct. 25, 1995

The present invention provides for a novel ligand that binds proteins belonging to the Eph subfamily of receptor-like protein tyrosine kinases, such as the Elk receptor and methods for making soluble forms of this ligand that are biologically active.

BACKGROUND OF THE INVENTION

The ability of polypeptide ligands to bind cells and thereby elicit a phenotypic response such as cell growth, survival or differentiation is often mediated through transmembrane tyrosine kinases. The extracellular portion of each receptor tyrosine kinase (RTK) is generally the most distinctive portion of the molecule, as it provides the protein with its ligand-recognizing characteristic. Binding of a ligand to the extracellular domain results in signal transduction via an intracellular tyrosine kinase catalytic domain which transmits a biological signal to intracellular target proteins. The particular array of sequence motifs of this cytoplasmic, catalytic domain determines its access to potential kinase substrates (Mohammadi, et al.,1990, Mol. Cell. Biol., 11: 5068–5078; Fantl, et al., 1992, Cell, 69:413–413).

RTKs appear to undergo dimerization or some related conformational change following ligand binding (Schlessinger, J., 1988, Trend Biochem. Sci. 13:443–447; Ullrich and Schlessinger, 1990, Cell, 61:203–212; Schlessinger and Ullrich, 1992, Neuron 9:383–391); molecular interactions between dimerizing cytoplasmic domains lead to activation of kinase function. In some instances, such as the growth factor platelet derived growth factor (PDGF), the ligand is a dimer that binds two receptor molecules (Hart, et al., 1988, Science, 240: 1529–1531; Heldin, 1989, J. Biol. Chem. 264:8905–8912) while, for example, in the case of EGF, the ligand is a monomer (Weber, et al., 1984, J. Biol. Chem., 259:14631–14636).

The tissue distribution of a particular tyrosine kinase receptor within higher organisms provides relevant data as to the biological function of the receptor. The tyrosine kinase receptors for some growth and differentiation factors, such as fibroblast growth factor (FGF) are widely expressed and therefore appear to play some general role in tissue growth and maintenance. Members of the Trk RTK family (Glass & Yancopoulos, 1993, Trends in Cell Biol, 3:262–268) of receptors are more generally limited to cells of the nervous system, and the Nerve Growth Factor family consisting of NGF, BDNF, NT-3 and NT-4/5 (known as the neurotrophins) which bind these receptors promote the differentiation of diverse groups of neurons in the brain and periphery (Lindsay, R. M, 1993, in Neurotrophic Factors, S. E. Loughlin & J. H. Fallon, eds., pp. 257–284 (San Diego, Calif.: Academic Press). The localization of one such Trk family receptor, trkB, in tissue provided some insight into the potential biological role of this receptor, as well as the ligands that bind this receptor (referred to herein as cognates). Thus, for example, in adult mice, trkB was found to be preferentially expressed in brain tissue, although significant levels of trkB mRNAs were also observed in lung, muscle, and ovaries. Further, trkB transcripts were detected in mid and late gestation embryos. In situ hybridization analysis of 14 and 18 day old mouse embryos indicated that trkB transcripts were localized in the central and peripheral nervous systems, including brain, spinal cord, spinal and cranial ganglia, paravertebral trunk of the sympathetic nervous system and various innervation pathways, suggesting that the trkB gene product may be a receptor involved in neurogenesis and early neural development as well as play a role in the adult nervous system.

The cellular environment in which an RTK is expressed may influence the biological response exhibited upon binding of a ligand to the receptor. Thus, for example, when a neuronal cell expressing a Trk receptor is exposed to a neurotrophin which binds that receptor, neuronal survival and differentiation results. When the same receptor is expressed by a fibroblast, exposure to the neurotrophin results in proliferation of the fibroblast (Glass, et al., 1991, Cell 66:405–413). Thus, it appears that the extracellular domain provides the determining factor as to the ligand specificity, and once signal transduction is initiated the cellular environment will determine the phenotypic outcome of that signal transduction.

A number of RTK families have been identified based on sequence homologies in their intracellular domain. The receptor and signal transduction pathways utilized by NGF involves the product of the trk proto-oncogene (Kaplan et al., 1991, Nature 350:156–160; Klein et al., 1991, Cell 65:189–197). Klein et al. (1989, EMBO J. 8:3701–3709) reported the isolation of trkB, which encodes a second member of the tyrosine protein kinase family of receptors found to be highly related to the human trk protooncogene. TrkB binds and mediates the functional responses to BDNF, NT-4, and, to a lesser extent, NT-3 (Squinto, et al., 1991, Cell 65:885–903; Ip, et al., 1992, Proc. Natl. Acad. Sci. U.S.A. 89:3060–3064; Klein, et al., 1992, Neuron, 8:947–956). At the amino acid level, the products of trk and trkB were found to share 57 percent homology in their extracellular regions, including 9 of the 11 cysteines present in trk. This homology was found to increase to 88 percent within their respective tyrosine kinase catalytic domains. The Trk gene family has now been expanded to include the trkC locus, with NT-3 having been identified as the preferred ligand for trkC (Lamballe, et al., 1991, Cell 66: 967–979; Valenzuela, et al. 1993, Neuron 10:963–974).

The Eph-related transmembrane tyrosine kinases comprise the largest known family of receptor-like tyrosine kinases, with many members displaying specific expression in the developing and adult nervous system. Two novel members of the Eph RTK family, termed Ehk (eph homology kinase) -1 and -2 were identified using a polymerase chain reaction (PCR)-based screen of genes expressed in brain (Maisonpierre, et al. 1993, Oncogene 8:3277–388). These genes appear to be expressed exclusively in the nervous system, with Ehk-1 expression beginning early in neural development. Recently, a new member of this group of related receptors, Ehk-3 has been cloned (Valenzuela, et al. 1995, Oncogene 10:1573–1580).

The elk gene encodes a receptorlike protein-tyrosine kinase that also belongs to the eph subfamily, and which is expressed almost exclusively in the brain (and at lower levels in the testes) (Letwin, et al. 1988; Oncogene 3:621–678; Lhotak, et al., 1991 Mol. Cell. Biol. 11: 2496–2502). Based on its expression profile, the Elk receptor and its cognate ligand are expected to play a role in cell to cell interactions in the nervous system. Other members of the Eph family of receptors that fall within the same subclass as Elk include the Nuk/Cek5, Hek2/Sek4 and Htk receptors (Brambilla and Klein, 1995, Mol. Cell. Neurosci., 6:487–495, Gale, et al., 1996, Neuron 17:9–19).

Unlike the Ehks and Elk receptors, the closely related Eck receptor appears to function in a more pleiotropic manner; it has been identified in neural, epithelial and skeletal tissues and it appears to be involved in the gastrulation, craniofacial, and limb bud sites of pattern formation in the mouse embryo (Ganju, et al. 1994, Oncogene 9:1613–1624).

The identification of a large number of receptor tyrosine kinases has far exceeded the identification of their cognate ligands. At best, determination of the tissues in which such receptors are expressed provides insight into the regulation of the growth, proliferation and regeneration of cells in target tissues. Because RTKs appear to mediate a number of important functions during development, their cognate ligands will inevitably play a crucial role in development.

Although a number of schemes have been devised for the identification of cognate ligands for the many orphan receptors that have been identified, very few such ligands have been identified, and the ligands that have been identified to date appear to have no activity other than the ability to bind their cognate receptor. For example, International Publication Number WO/94/11020 published on May 26, 1994 describes ligands that bind to the Eck receptor. In particular the ligand EBP (also known as B61) is described. However, although binding of B61 to the Eck receptor is disclosed, no biological activity is described. Similarly, despite the description in PCT Publication Number W094/11384 (published May 26, 1994) of a ligand that binds the Elk receptor, no biological activity was observed, regardless of whether the ligand was presented as membrane bound or in the form of an Fc dimer of the soluble ligand. With respect to the Elk receptor, however, chimeric EGFR-Elk receptors (having the extracellular domain of the EGFR fused to the Elk cytoplasmic domain) have been used to demonstrate the functional integrity (as measured by EGF-stimulated autophosphorylation) of the enzymatic domain of this receptor. (Lhotak and Pawson, 1993, Mol. Cell. Biol. 13:7071–7079).

SUMMARY OF THE INVENTION

The present invention, provides for a novel polypeptide ligand, designated as Efl-6, that binds to the Elk, Nuk/Cek5, Hek2/Sek4, Htk, and Sek1 receptors on cells. More importantly, the invention provides a means of making biologically active, soluble forms of this ligand, which are useful in promoting a differential function and/or influencing the phenotype, such as growth and/or proliferation, of receptor bearing cells. The invention also provides for nucleic acids encoding such polypeptide ligands, and both prokaryotic and eukaryotic expression systems for producing such proteins. The invention also provides for antibodies to these ligands.

According to the invention, soluble forms of the ligands described herein may be used to promote biological responses in Elk, Nuk/Cek5, Hek2/Sek4, Htk, and Sek1 receptor-expressing cells. In particular, a general method is described herein which produces "clustering" of ligands for eph-related receptors, which functions to make otherwise inactive soluble ligands biologically active, or which enhances the biological activity of ligands that, absent such clustering, would have only low levels of biological activity.

The ligands described herein also have diagnostic utilities. In particular embodiments of !the invention, methods of detecting aberrancies in their function or expression may be used in the diagnosis of neurological or other disorders.

In other embodiments, manipulation of the interaction between the ligands and their cognate receptor may be used in assay systems designed to identify both agonists and antagonists of Eph receptor ligands. Such agonists and antagonists may be developed for use in the eventual treatment of neurological or other disorders.

BRIEF DESCRIPTION OF THE FIGURES

FIG. 1A and FIG. 1F Nucleotide (SEQ. ID NO. 1) and encoded protein (SEQ. ID NO. 2) sequence of Efl-6. The putative signal sequence is encoded by about nucleotide 202 to about nucleotide 273. The coding region of the mature protein begins at about nucleotide 274 and ends at about nucleotide 1224. The deposited clone has an A at position 698. This change created an amino acid change from Q (Gln) to R (Arg). The coding region for the putative transmembrane domain is shown underlined. The amino acid sequence of the encoded extracellular domain, which is encoded by about nucleotide 274 to about nucleotide 873, is shown in bold letters.

DETAILED DESCRIPTION OF THE INVENTION

The present invention provides for a novel polypeptide ligand that binds to the Elk receptor. The novel polypeptide ligand of the present invention is also able to bind other members of the Elk subclass of Eph receptors, including Nuk/Cek5, Hek2/Sek4 and Htk, as well as the only receptor known to "cross subclasses", known as Sek1 (Brambilla and Klein, 1995, Mol. Cell. Neurosci., 6:487–495, Gale, et al., 1996, Neuron 17:9–19). Accordingly, as used herein, the "Elk" receptor refers to Elk, as well as the above receptors known to bind the Elk ligands.

The invention further provides a means of making biologically active, soluble forms of the Efl-6 ligand, which are useful in promoting a differential function and/or influencing the phenotype, such as growth and/or proliferation, of receptor bearing cells. The invention also provides for nucleic acids encoding such a polypeptide ligand, and both prokaryotic and eukaryotic expression systems for producing this protein. The invention also provides for antibodies to this ligand.

The novel ligand described herein is designated as Efl (Eph transmembrane tyrosine kinase family ligands)-6. A deposit designated as pbluescript SK⁻ encoding Efl-6 was made with the American Type Culture Collection on Oct. 19, 1995 and has received accession number 97319.

According to the invention, soluble forms of the Elk ligand (referred to herein as Efl-6) may be used to promote biological responses in Elk receptor-expressing cells. In particular, a general method is described herein which produces "clustering" of Efl-6 ligand which functions to make otherwise inactive soluble ligand biologically active, or which enhances the biological activity of the ligand which, absent such clustering, would have only low levels of biological activity.

The Efl-6 ligand described herein may also have diagnostic utilities. In particular embodiments of the invention, methods of detecting aberrancies in its function or expression may be used in the diagnosis of neurological or other disorders. In other embodiments, manipulation of the interaction between the ligand and its cognate receptor may be used in the treatment of neurological or other disorders.

When used herein, Efl-6 includes functionally equivalent molecules in which amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may, be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

Cells that express Efl-6 may do so naturally or may be genetically engineered to produce this ligand, as described supra, by transfection, transduction, electroporation, microinjection, via a transgenic animal, etc. of nucleic acid encoding Efl-6 described herein in a suitable expression vector. A vector containing the cDNA encoding for EFl-6 deposited with the American Type Culture Collection under the terms of the Budapest Treaty on Oct. 19, 1995 as pBluescriptSK-Efl-6 has been given the ATCC designation 97319.

The present invention encompasses the DNA sequence contained in the above deposited plasmid, as well as DNA and RNA sequences that hybridize to the Efl-6 encoding sequence contained therein, under conditions of moderate stringency, as defined in, for example, Sambrook, et al. Molecular Cloning: A Laboratory Manual, 2 ed. Vol. 1, pp. 101–104, Cold Spring Harbor Laboratory Press (1989). Thus, nucleic acids contemplated by the invention include the sequence as contained in the deposit and as set forth in FIG. 1A and FIG. 1B (SEQ. ID. NO. 1), sequences of nucleic acids that hybridize to such sequence and which bind the Elk receptor, and nucleic acid sequences which are degenerate of the above sequences as a result of the genetic code, but which encode ligand(s) that bind the Elk receptor.

In addition, the present invention contemplates use of the ligands described herein in soluble forms, truncated forms, and tagged forms. This includes monomeric forms of the ligand which may bind to the receptor and function as an antagonist.

Any of the methods known to one skilled in the art for the insertion of DNA fragments into a vector may be used to construct expression vectors encoding Efl-6 using appropriate transcriptional/translational control signals and the protein coding sequences. These methods May include in vitro recombinant DNA and synthetic techniques and in vivo recombinations (genetic recombination). Expression of nucleic acid sequence encoding the Efl-6 or peptide fragments thereof may be regulated by a second nucleic acid sequence so that the protein or peptide is expressed in a host transformed with the recombinant DNA molecule. For example, expression of the Efl-6 described herein may be controlled by any promoter/enhancer element known in the art. Promoters which may be used to control expression of the ligands include, but are not limited to the long terminal repeat as described in Squinto et al., (1991, Cell 65:1–20); the SV40 early promoter region (Bernoist and Chambon, 1981, Nature 290:304–310), the CMV promoter, the M-MuLV 5' terminal repeat the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothioein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25), see also "Useful proteins from recombinant bacteria" in Scientific American, 1980, 242:74–94; promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift, et al., 1984, Cell 38:639–646; Ornitz, et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl, et al., 1984, Cell 38:647–658; Adames, et al., 1985, Nature 318:533–538; Alexander et al., 1987, Mol. Cell. Biol. 7:1436–1444), mouse mammary tumor virus control region which is active in testicular, breast, lymphoid and mast cells (Leder, et al., 1986, Cell 45:485–495), albumin gene control region which is active in liver (Pinkert, et al., 1987, Genes and Devel. 1:268–276), alpha-fetoprotein gene control region which is active in liver (Krumlauf, et al., 1985, Mol. Cell. Biol. 5:1639–1648; Hammer et al., 1987, Science 235:53–58); alpha 1-antitrypsin gene control region which is active in the liver (Kelsey, et al, 1987, Genes and Devel. 1:161–171), beta-globin gene control region which is active in myeloid cells (Mogram, et al., 1985, Nature 315:338–340; Kollias, et al., 1986, Cell 46:89–94); myelin basic protein gene control region which is active in oligodendrocyte cells in the brain (Readhead, et al., 1987, Cell 48:703–712); myosin light chain-2 gene control region which is active in skeletal muscle (Shani, 1985, Nature 314:283–286), and gonadotropic releasing hormone gene control region which is active in the hypothalamus (Mason et al., 1986, Science 234:1372–1378).

Thus, according to the invention, expression vectors capable of being replicated in a bacterial or eukaryotic host comprising Efl-6 encoding nucleic acid as described herein, are used to transfect the host and thereby direct expression of such nucleic acid to produce the Efl-6 proteins, which may then be recovered in biologically active form. As used herein, a biologically active form includes a form capable of binding to the relevant receptor, such as Elk, and causing a differentiated function and/or influencing the phenotype of the cell expressing the receptor. Such biologically active forms would, for example, induce phosphorylation of the tyrosine kinase domain of the Elk receptor, or stimulation of synthesis of cellular DNA. Alternatively, biologically active Elf-6 ligand includes monomeric forms that bind the receptor and act as antagonists.

Expression vectors containing the gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to an inserted efl-6 gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the efl-6 gene is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of the efl-6 gene product, for example, by binding of the ligand to the Elk receptor or portion thereof which may be tagged with, for example, a detectable antibody or portion thereof or binding to antibodies produced against the Efl-6 protein or a portion thereof.

Efl-6 appears to be a conventional transmembrane protein with a cytoplasmic domain. The transmembrane domain is shown underlined in FIG. 1A and 1B (SEQ. ID. NO. 2 ). Accordingly, the soluble or extracellular domain of the ligand (sEfl-6) is encoded by the nucleotide sequence from about nucleotide 274 to about nucleotide 873.

The ligands described herein may be produced as membrane bound forms in animal cell expression systems or may be expressed in soluble form. Soluble forms of the ligands may be expressed using methods known to those in the art. A commonly used strategy involves use of oligonucleotide primers, one of which spans the N-terminus of the protein, the other of which spans the region just upstream to a hydrophobic segment of the protein, which represents either the GPl-linkage recognition domain or a transmembrane domain of the protein. The oligonucleotide spanning the C-terminus region is modified so as to contain a stop codon prior to the hydrophobic domain. The two oligonucleotides are used to amplify a modified version of the gene-encoding a protein that is secreted instead of membrane bound. Alternatively, a convenient restriction site in the vector can be used to insert an altered sequence that removes the GPI-linkage recognition domain or transmembrane domain, thus resulting in a vector capable of expressing a secreted form of the protein. The soluble protein so produced would include the region of the protein from, the N-terminus to the region preceding the hydrophobic GPI recognition domain or transmembrane domain.

Applicants have discovered that although the soluble ligands produced according to the invention bind to the receptors in the eph subfamily, such soluble ligands often have little or no biological activity. Such soluble ligands are activated, according to the present invention, by ligand "clustering". "Clustering" as used herein refers to any method known to one skilled in the art for creating multimers of the soluble portions of ligands described herein.

In one embodiment, a "clustered" efl-6 is a dimer, made for example, according to the present invention utilizing the Fc domain of IgG (Aruffo, et al., 1991, Cell 67:35–44), which results in the expression of the soluble ligand as a disulfide-linked homodimer. In another embodiment, secreted forms of the ligand are constructed with epitope tags at their C-termini; anti-tag antibodies are then used to aggregate the ligands.

In addition, the invention contemplates other "engineered" ligand molecules that exist as or form multimers. For example, dimers of the extracellular domains may be engineered using leucine zippers. The leucine zipper domains of the human transcription factors c-jun and c-fos have been shown to form stable heterodimers [Busch and Sassone-Corsi, Trends Genetics 6: 36–40 (1990); Gentz, et al., Science 243: 1695–1699 (1989)] with a 1:1 stoichiometry. Although jun-jun homodimers have also been shown to form, they are about 1000-fold less stable than jun-fos heterodimers. Fos-fos homodimers have not been detected. The leucine zipper domain of either c-jun or c-fos are fused in frame at the C-terminus of the soluble or extracellular domains of the above mentioned ligands by genetically engineering chimeric genes. The fusions may be direct or they may employ a flexible linker domain, such as the hinge region of human IgG, or polypeptide linkers consisting of small amino acids, such as glycine, serine, threonine or alanine, at various lengths and combinations. Additionally, the chimeric proteins may be tagged by His-His-His-His-His-His (His6)(SEQ. ID. NO. 3), to allow rapid purification by metal-chelate chromatography, and/or by epitopes to which antibodies are available, to allow for detection on western blots, immunoprecipitation, or activity depletion/blocking in bioassays.

Alternatively, multimers may be made by genetically engineering and expressing molecules that consist of the soluble or extracellular portion of the ligand followed by the Fc-domain of hIgG, followed by either the c-jun or the c-fos leucine zippers described above [Kostelny, et. al., J. Immunol. 148: 1547–1553 (1992)]. Since these leucine zippers form predominately heterodimers, they may be used to drive formation of the heterodimers where desired. As for the chimeric proteins described using leucine zippers, these may also be tagged with metal chelates or an epitope. This tagged domain can be used for rapid purification by metal-chelate chromatography, and/or by antibodies, to allow for detection on western blots, immunoprecipitation, or activity depletion/blocking in bioassays.

In another embodiment of the invention, multimeric soluble ligands are prepared by expression as chimeric molecules utilizing flexible linker loops. A DNA construct encoding the chimeric protein is designed such that it expresses two or more soluble or extracellular domains fused together in tandem ("head to head") by a flexible loop. This loop may be entirely artificial (e.g. polyglycine repeats interrupted by serine or threonine at a certain interval) or "borrowed" from naturally occurring proteins (e.g. the hinge region of hIgG). Molecules may be engineered in which the length and composition of the loop is varied, to allow for selection of molecules with desired characteristics. Although not wishing to be bound by theory, applicants believe that membrane attachment of the ligands facilitates ligand clustering, which in turn promotes receptor multimerization and activation. Thus, according to the invention, biological activity of, the soluble ligand is achieved by mimicking, in solution, membrane associated ligand clustering. Thus, a biologically active, clustered soluble eph family ligand comprises (soluble Efl)$_n$, wherein the soluble efl is the extracellular domain of a ligand that binds, an eph family receptor and n is 2 or greater. As described herein, Efl-6 is made biologically active according to the process of the invention.

In each case, one skilled in the art will recognize that the success of clustering will require analysis of the biological activity utilizing bioassays such as those described herein. For example, receptor phosphorylation induced by stimulating receptor expressing reporter cells with COS cells, overexpressing membrane forms of the ligands, soluble forms of the ligands and clustered ligands may be compared.

Although in some instances dimerization of the ligand is sufficient to induce biological activity, in certain instances, the methods described herein are used to determine the sufficiency of a particular clustering technique. Often dimerization of a soluble ligand utilizing Fc appears to, be insufficient for achieving a biological response, yet further clustering of the ligand according to the invention using anti-Fc antibodies may result in a substantial increase in biological activity.

Cells of the present; invention may transiently or, preferably, constitutively and permanently express Efl-6 in native form, or in soluble form as tagged Efl-6 or clustered Efl-6 as described herein.

The recombinant factor may be purified by any technique which allows for the subsequent formation of a stable, biologically active protein. For example, and not by way of limitation, the factor may be recovered from cells either as a soluble protein or as inclusion bodies, from which lit may be extracted quantitatively by 8M guanidinium hydrochloride and dialysis. In order to further purify the factor, conventional ion exchange chromatography, hydrophobic interaction chromatography, reverse phase chromatography or gel filtration may be used.

In additional embodiments of the invention, recombinant efl-6 may be used to inactivate or "knock out" the endogenous gene by homologous recombination, and thereby create an Efl-6 protein deficient cell, tissue, or animal. For example, and not by way of limitation, recombinant efl may be engineered to contain an insertional mutation, for example the neo gene, which would inactivate the native efl-6 gene. Such a construct, under the control of a suitable promoter, may be introduced into a cell, such as an embryonic stem cell, by a technique such as transfection, transduction, injection, etc. Cells containing the construct may then be selected by G418 resistance. Cells which lack an intact efl-6 may then be identified, e.g. by Southern blotting or Northern blotting or assay of expression. Cells lacking an intact efl-6 may then be fused to early embryo cells to generate transgenic animals deficient in such ligand. A comparison of such an animal with an animal expressing endogenous Efl-6 would aid in the elucidation of the role of the ligands in development and maintenance. Such an animal may be used to define specific neuronal populations, or any other in vivo processes, normally dependent upon the ligand.

The present invention also provides for antibodies to the Efl-6 described herein which are useful for detection of the ligand in, for example, diagnostic applications. Antibodies to the ligand may also be useful for achieving clustering according to the invention. In instances where endogenous ligand exists, the antibody itself may act as the therapeutic by activating existing ligand.

For preparation of monoclonal antibodies directed toward Efl-6, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor, et al., 1983, Immunology Today 4:72), and the EBV-hybridoma technique to produce human monoclonal antibodies (Cole, et al., 1985, in "Monoclonal Antibodies and Cancer Therapy," Alan R. Liss, Inc. pp. 77–96) and the like are within the, scope of the present invention.

The monoclonal antibodies for diagnostic or therapeutic use may be human monoclonal antibodies or chimeric human-mouse (or other species) monoclonal antibodies. Human monoclonal antibodies may be made by any of numerous techniques known in the art (e.g., Teng, et al., 1983, Proc. Natl. Acad. Sci. U.S.A. 80:7308–7312; Kozbor, et al., 1983, Immunology Today 4:72–79; Olsson, et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of the Efl-6 described herein. For the production of antibody, various host animals can be immunized by injection with the Efl-6, or a fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and Corynebacterium Parvum A molecular clone of an antibody to a selected Efl-6 epitope can be prepared by known techniques. Recombinant DNA methodology (see e.g., Maniatis, et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

The present invention provides for antibody molecules as well as fragments of such antibody molecules. Antibody fragments which contain the idiotype of the molecule can be generated by known Techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

The present invention also provides for methods of treating a patient suffering from a neurological disorder comprising treating the patient with an effective amount of Efl-6, peptide fragments thereof, or derivatives thereof capable of binding to Elk receptor.

The Elk receptor is also expressed primarily in brain. Accordingly, it is believed that the Elk binding ligand described herein will support the induction of a differential function and/or influence the phenotype, such as growth and/or survival of neural cells, expressing this receptor. As described in Gale, et al., 1996, Oncogene 13:1343–1352, Elk-6 (described as Elk ligand 3 in the reference) is notable for its remarkable restricted and prominent expression in the floor plate and roof plate of the developing neural tube and its rhombomere-specific expression in the developing hindbrain. This distribution suggests a role of Efl-6 and its reciprocal receptor, in neuronal guidance and boundary formation, critical features in the organization of the developing vertebrate central nervous system.

The present invention also provides for pharmaceutical compositions comprising the Efl-6 described herein, peptide fragments thereof, or derivatives in a suitable pharmacologic carrier.

The Efl-6 proteins, peptide fragments, or derivatives may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

As our understandin of neurodegenerative disease/ neurotrauma becomes clearer, it may become apparent that it would be beneficial to decrease the effect of endogenous Efl-6. Therefore, in areas of nervous system trauma, it may be desirable to provide Efl-6 antagonists, including, but not limited to, soluble forms of Efl-6 which may compete with cell-bound ligand for interaction with Elk receptor. Alternatively, soluble forms of the Elk receptors (e.g. expressed as "receptorbodies" produced as described herein) may act as antagonists by binding, and thereby inactivating the ligand. It may be desirable to provide such antagonists locally at the injury site rather than systemically. Use of an Efl-6 antagonist providing implant may be desirable.

Alternatively, certain conditions may benefit from an increase in Efl-6 responsiveness. It may therefore be beneficial to increase the number or binding affinity of Efl-6 in patients suffering from such conditions. This could be achieved through gene therapy using either Efl-6, Efl-6 expressing cells, or Elk receptor or receptor chimeras (cells expressing the extracellular domain of the Elk receptor). Selective expression of such recombinant proteins in appropriate cells could be achieved using their encoding genes controlled by tissue specific or inducible promoters or by producing localized infection with replication defective viruses carrying the recombinant genes.

The Efl-6 encoding DNA as deposited with the ATCC and having accession number 97319 was isolated from a Stratagene (La Jolla, Calif.) human brain, (frontal cortex) library (Catalogue No. 936212). The library is in the λZAPII vector. The sequence of the Efl-6 coding region of this vector is set forth in FIG. 1A and 1B (SEQ. ID. NO. 1) Assays or purification of the Efl-6 protein may be conducted by use of an Elk receptorbody, which consists of the extracellular domain of Elk fused to the IgG1 constant region. This receptorbody is prepared as follows: The Fc portion of human IgG1, starting from the hinge region and extending to the carboxy terminus of the molecule, was cloned from placental cDNA using PCR with oligonucleotides corresponding to the published sequence of human IgG1. Convenient restriction sites were also incorporated into the oligonucleotides so as to allow cloning of the PCR fragment into an expression vector. Expression vectors containing full length receptors were modified either by restriction enzyme digests or by PCR strategies so as to replace the transmembrane and intracellular domains with restriction sites that allow cloning the human IgG1 fragment into these sites; this was done in such a way as to generate a fusion protein with the receptor ectodomain as its amino-terminus and the Fc portion of human IgG1 as its carboxy-terminus. An alternative method of preparing receptorbodies is described in Goodwin, et. al. 193 Cell 73:447–456.

Deposit of Microorganisms

The following vector been deposited with the American Type Culture Collection, 10801 University Boulevard, Manassas, Va. 20110-2209 in accordance with the Budapest Treaty.

DEPOSIT ACCESSION NUMBER pBluescript SK⁻ Efl-6 97319

The present invention is not to be limited in scope by the specific embodiments described herein. Indeed, various modifications of the invention in addition to those described herein will become apparent to those, skilled in the art from the foregoing description and accompanying figures. Such modifications are intended to fall within the scope of the appended claims.

Various references are cited herein, the disclosures of which are incorporated by reference in their entireties.

What is claimed is:

1. An isolated and purified nucleic acid molecule encoding Efl-6 protein wherein the sequence of said nucleic acid is selected from the group consisting of:
   (a) the sequence of the DNA encoding mature Efl-6 protein contained in the plasmid pBluescriptSK-Efl-6 as deposited with the American Type Culture Collection on Oct. 19, 1995 and designated as 97319;
   (b) the sequence of the DNA encoding mature Efl-6 protein as set forth in FIG. 1A and FIG. 1B (SEQ ID NO: 1);
   (c) DNA sequences that are degenerate as a result of the genetic code to a DNA sequence of (a) or (b) and which encode an Efl-6 protein that binds a member of the Elk subclass of Eph receptors.

2. Isolated and purified mature Efl-6 protein having an amino acid sequence as set forth in FIG. 1A and FIG. 1B (SEQ ID NO: 2).

3. An isolated nucleic acid encoding the extracellular domain of Efl-6 (sEfl-6) having a sequence selected from the following:
   (a) the sequence set forth from about nucleotide 274 to about nucleotide 873 of FIG. 1A and FIG. 1B (SEQ. ID. NO. 1); and
   (b) a sequence which encodes the extracellular domain of Efl-6 as set forth in FIG. 1A and FIG. 1B (SEQ. ID. NO. 1).

4. Purified sEfl-6 encoded by the nucleotide sequence of claim 3.

5. (sEfl-6)n comprising the sEfl-6 protein according to claim 4, wherein n is 2 or greater.

6. An Efl-6 protein comprising soluble Efl-6 protein according to claim 4 and the Fc portion of IgG.

7. A vector which comprises a nucleic acid molecule of claim 1.

8. A vector according to claim 7 wherein the nucleic acid molecule is operatively linked to an expression control sequence capable of directing its expression in a host cell.

9. A host cell containing a vector according to claim 8.

10. A vector which comprises a nucleic acid molecule of claim 3.

11. A vector according to claim 10 wherein the nucleic acid molecule is operatively linked to an expression control sequence capable of directing its expression in a host cell.

12. A host cell containing a vector according to claim 11.

13. A method of producing Efl-6 ligand which comprises growing cells of a host according to claim 8 under conditions permitting production of the ligand, and recovering the ligand so produced.

14. A method of producing Efl-6 soluble ligand which comprises growing cells of a host according to claim 11 under conditions permitting production of the ligand, and recovering the ligand so produced.

* * * * *

SEQUENCE LISTING

```
<160> NUMBER OF SEQ ID NOS: 3

<210> SEQ ID NO 1
<211> LENGTH: 1860
<212> TYPE: DNA
<213> ORGANISM: Homo sapiens
<220> FEATURE:
<221> NAME/KEY: CDS
<222> LOCATION: (202)..(1224)
<220> FEATURE:
<221> NAME/KEY: modified_base
<222> LOCATION: (1717)
<223> OTHER INFORMATION: n=a, c, g, or t
<220> FEATURE:
<221> NAME/KEY: modified_base
<222> LOCATION: (1741)
<223> OTHER INFORMATION: n=a, c, g or t
<220> FEATURE:
<221> NAME/KEY: modified_base
<222> LOCATION: (1782)
<223> OTHER INFORMATION: n=a, c, g, or t
<220> FEATURE:
<221> NAME/KEY: modified_base
<222> LOCATION: (1795)
<223> OTHER INFORMATION: n=a, c, g, or t

<400> SEQUENCE: 1
gaattcccac cccgggatct gtgagactga gcgctctgcc gcgggggcgc gggcacagca      60
ggaarcaggt ccgcgtgggc gctgggggca tcagctaccg gggtggtccg ggctgaagag     120
ccaggcagcc aaggcagcca ccccgggggg tgggcgactt tggggagtt ggtgccccgc      180
```

```
cccccaggcc ttggcgggt c atg ggg ccc ccc cat tct ggg ccg ggg ggc     231
                       Met Gly Pro Pro His Ser Gly Pro Gly Gly
                        1               5                    10 gtg cga gtc ggg gcc ctg ctg ctg ggg gtt ttg ggg ctg gtg tct         279
Val Arg Val Gly Ala Leu Leu Leu Gly Val Leu Gly Leu Val Ser
                15                  20                  25 ggg ctc agc ctg gag cct gtc tac tgg aac tcg gcg aat aag agg ttc     327
Gly Leu Ser Leu Glu Pro Val Tyr Trp Asn Ser Ala Asn Lys Arg Phe
            30                  35                  40 cag gca gag ggt ggt tat gtg ctg tac cct cag atc ggg gac cgg cta     375
Gln Ala Glu Gly Gly Tyr Val Leu Tyr Pro Gln Ile Gly Asp Arg Leu
        45                  50                  55 gac ctg ctc tgc ccc cgg gcc cgg cct cct ggc cct cac tcc tct cct     423
Asp Leu Leu Cys Pro Arg Ala Arg Pro Pro Gly Pro His Ser Ser Pro
    60                  65                  70 aat tat gag ttc tac aag ctg tac ctg gta ggg ggt gct cag ggc cgg     471
Asn Tyr Glu Phe Tyr Lys Leu Tyr Leu Val Gly Gly Ala Gln Gly Arg
75                  80                  85                  90 cgc tgt gag gca ccc cct gcc cca aac ctc ctt ctc act tgt gat cgc     519
Arg Cys Glu Ala Pro Pro Ala Pro Asn Leu Leu Leu Thr Cys Asp Arg
                95                  100                 105 cca gac ctg gat ctc cgc ttc acc atc aag ttc cag gag tat agc cct     567
Pro Asp Leu Asp Leu Arg Phe Thr Ile Lys Phe Gln Glu Tyr Ser Pro
            110                 115                 120 aat ctc tgg ggc cac gag ttc cgc tcg cac cac gat tac tac atc att     615
Asn Leu Trp Gly His Glu Phe Arg Ser His His Asp Tyr Tyr Ile Ile
        125                 130                 135 gcc aca tcg gat ggg acc cgg gag ggc ctg gag agc ctg cag gga ggt     663
Ala Thr Ser Asp Gly Thr Arg Glu Gly Leu Glu Ser Leu Gln Gly Gly
    140                 145                 150 gtg tgc cta acc aga ggc atg aag gtg ctt ctc cra gtg gga caa agt     711
Val Cys Leu Thr Arg Gly Met Lys Val Leu Leu Xaa Val Gly Gln Ser
155                 160                 165                 170 ccc cga gga ggg gct gtc ccc cga aaa cct gtg tct gaa atg ccc atg     759
Pro Arg Gly Gly Ala Val Pro Arg Lys Pro Val Ser Glu Met Pro Met
                175                 180                 185 gaa aga gac cga ggg gca gcc cac agc ctg gag cct ggg aag gag aac     807
Glu Arg Asp Arg Gly Ala Ala His Ser Leu Glu Pro Gly Lys Glu Asn
            190                 195                 200 ctg cca ggt gac ccc acc agc aat gca acc tcc cgg ggt gct gaa ggc     855
Leu Pro Gly Asp Pro Thr Ser Asn Ala Thr Ser Arg Gly Ala Glu Gly
        205                 210                 215 ccc ctg ccc cct ccc agc atg cct gca gtg gct ggg gca gca ggg ggg     903
Pro Leu Pro Pro Pro Ser Met Pro Ala Val Ala Gly Ala Ala Gly Gly
    220                 225                 230 ctg gcg ctg ctc ttg ctg ggc gtg gca ggg gct ggg gtg gcc atg tgt     951
Leu Ala Leu Leu Leu Leu Gly Val Ala Gly Ala Gly Val Ala Met Cys
235                 240                 245                 250 tgg cgg aga cgg cgg gcc aag cct tcg gag agt cgc cac cct ggt cct     999
Trp Arg Arg Arg Arg Ala Lys Pro Ser Glu Ser Arg His Pro Gly Pro
                255                 260                 265 ggc tcc ttc ggg agg gga ggg tct ctg ggc ctg ggg ggt gga ggt ggg     1047
Gly Ser Phe Gly Arg Gly Gly Ser Leu Gly Leu Gly Gly Gly Gly Gly
            270                 275                 280 atg gga cct cgg gag gct gag cct ggg gag cta ggg ata gct ctg cgg     1095
Met Gly Pro Arg Glu Ala Glu Pro Gly Glu Leu Gly Ile Ala Leu Arg
        285                 290                 295 ggt ggc ggg gct gca gat ccc ccc ttc tgc ccc cac tat gag aag gtg     1143
Gly Gly Gly Ala Ala Asp Pro Pro Phe Cys Pro His Tyr Glu Lys Val
    300                 305                 310
```

-continued

```
agt ggt gac tat ggg cat cct gtg tat atc gtg cag gat ggg ccc ccc     1191
Ser Gly Asp Tyr Gly His Pro Val Tyr Ile Val Gln Asp Gly Pro Pro
315                 320                 325                 330 cag agc cct cca aac atc tac tac aag gta tga gggctcctct cacgtggcta   1244
Gln Ser Pro Pro Asn Ile Tyr Tyr Lys Val
                335                 340 tcctgaatcc agcccttctt ggggtgctcc tccagtttaa ttcctggttt gagggacacc   1304
tctaacatct cggcccccctg tgcccccca gcccttcac tcctcccggc tgctgtcctc    1364
gtctccactt ttaggattcc ttaggattcc cactgcccca cttcctgccc tcccgtttgg   1424
ccatgggtgc cccctctgt ctcagtgtcc ctggatcctt tttccttggg gaggggcaca    1484
ggctcagcct cctctctgac catgacccag gcatccttgt cccctcacc cacccagagc    1544 taggggcggg aacagcccac cttttggttg gcaccgcctt ctttctgcct ctcactggtt   1604
ttctcttctc tatctcttat tctttccctc tcttccgtct ctaggtctgt tcttcttccc   1664
tagcatcctc ctccccacat ctcctttcac cctcttggct tcttatcctg tgnctctccc   1724
atctcctggg tgggggnatc aaagcatttc tcccttagc tttcagcccc cttctganct   1784
ctcataccaa ncactcccct cagtctgtca aaaatggggg gcttatgggg aagggtctga   1844
caatccaccc caggtc                                                   1860
```

<210> SEQ ID NO 2
<211> LENGTH: 340
<212> TYPE: PRT
<213> ORGANISM: Homo sapiens
<220> FEATURE:
<221> NAME/KEY: site
<222> LOCATION: (166)
<223> OTHER INFORMATION: Xaa=Arg or Gln

<400> SEQUENCE: 2

```
Met Gly Pro Pro His Ser Gly Pro Gly Gly Val Arg Val Gly Ala Leu
  1               5                  10                  15

Leu Leu Gly Val Leu Gly Leu Val Ser Gly Leu Ser Leu Glu Pro
                 20                  25                  30

Val Tyr Trp Asn Ser Ala Asn Lys Arg Phe Gln Ala Glu Gly Gly Tyr
             35                  40                  45

Val Leu Tyr Pro Gln Ile Gly Asp Arg Leu Asp Leu Leu Cys Pro Arg
         50                  55                  60

Ala Arg Pro Pro Gly Pro His Ser Ser Pro Asn Tyr Glu Phe Tyr Lys
 65                  70                  75                  80

Leu Tyr Leu Val Gly Gly Ala Gln Gly Arg Arg Cys Glu Ala Pro Pro
                 85                  90                  95

Ala Pro Asn Leu Leu Leu Thr Cys Asp Arg Pro Asp Leu Asp Leu Arg
            100                 105                 110

Phe Thr Ile Lys Phe Gln Glu Tyr Ser Pro Asn Leu Trp Gly His Glu
        115                 120                 125

Phe Arg Ser His His Asp Tyr Tyr Ile Ile Ala Thr Ser Asp Gly Thr
    130                 135                 140

Arg Glu Gly Leu Glu Ser Leu Gln Gly Gly Val Cys Leu Thr Arg Gly
145                 150                 155                 160

Met Lys Val Leu Leu Xaa Val Gly Gln Ser Pro Arg Gly Gly Ala Val
                165                 170                 175

Pro Arg Lys Pro Val Ser Glu Met Pro Met Glu Arg Asp Arg Gly Ala
            180                 185                 190
```

```
Ala His Ser Leu Glu Pro Gly Lys Glu Asn Leu Pro Gly Asp Pro Thr
        195                 200                 205

Ser Asn Ala Thr Ser Arg Gly Ala Glu Gly Pro Leu Pro Pro Pro Ser
    210                 215                 220

Met Pro Ala Val Ala Gly Ala Ala Gly Gly Leu Ala Leu Leu Leu Leu
225                 230                 235                 240

Gly Val Ala Gly Ala Gly Gly Ala Met Cys Trp Arg Arg Arg Arg Ala
                245                 250                 255

Lys Pro Ser Glu Ser Arg His Pro Gly Pro Gly Ser Phe Gly Arg Gly
                260                 265                 270

Gly Ser Leu Gly Leu Gly Gly Gly Gly Met Gly Pro Arg Glu Ala
            275                 280                 285

Glu Pro Gly Glu Leu Gly Ile Ala Leu Arg Gly Gly Gly Ala Ala Asp
    290                 295                 300

Pro Pro Phe Cys Pro His Tyr Glu Lys Val Ser Gly Asp Tyr Gly His
305                 310                 315                 320

Pro Val Tyr Ile Val Gln Asp Gly Pro Pro Gln Ser Pro Pro Asn Ile
                325                 330                 335

Tyr Tyr Lys Val
        340

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: peptide tag

<400> SEQUENCE: 3

His His His His His His
  1               5
```